United States Patent [19]
Duke

[11] 3,948,968

[45] Apr. 6, 1976

[54] PREPARATION OF NITRILES FROM CARBOXYLIC ACIDS

[75] Inventor: Roy B. Duke, Littleton, Colo.

[73] Assignee: Marathon Oil Company, Findlay, Ohio

[22] Filed: Apr. 14, 1975

[21] Appl. No.: 567,670

Related U.S. Application Data

[63] Continuation-in-part of Ser. No. 386,788, Aug. 8, 1973, abandoned.

[52] U.S. Cl. .......................... 260/465 B; 260/465.2
[51] Int. Cl.² ...................................... C07C 120/08
[58] Field of Search ...................... 260/465 B, 465.2

[56] References Cited
UNITED STATES PATENTS

| | | | |
|---|---|---|---|
| 2,387,435 | 10/1945 | Fleysher | 260/465 |
| 3,076,014 | 1/1963 | Kroeper et al. | 260/465 |
| 3,317,585 | 5/1967 | Herschmann | 260/465.2 |

*Primary Examiner*—Lewis Gotts
*Assistant Examiner*—Dolph H. Torrence
*Attorney, Agent, or Firm*—Joseph C. Herring; Jack L. Hummel

[57] ABSTRACT

Nitriles are produced from carboxylic acids and ammonia utilizing an intermediate nitrogenous base-carboxylic acid complex by reacting said complex with ammonia at a temperature of from about 200° to about 800°C. The nitrogenous base is de-complexed as the nitriles are produced, recovered and recycled.

10 Claims, No Drawings

PREPARATION OF NITRILES FROM CARBOXYLIC ACIDS

CROSS REFERENCE TO RELATED APPLICATION

This application is a continuation-in-part of U.S. patent application Ser. No. 386,788 filed Aug. 8, 1973 and now abandoned.

BACKGROUND OF THE INVENTION

1. Field of the Invention

This invention relates to the general field of the production of nitriles, and specifically to the production of nitriles from corresponding carboxylic acids.

2. Description of the Prior Art

The preparation of nitriles from carboxylic acids and ammonia is well known. Catalysts which have been used include bauxite (Heinemann, et al., Industrial Engineering Chemistry, 41, 2928-31 (1949)); aluminum oxide at 200°-400°C (USSR Pat. No. 260,628); phosphates (Swiss Pat. No. 351,263); phosphates (German Pat. No. 1,046,015); and silica gel at 400°-500°C (Organic Synthesis, Vol. IV, page 62).

The above reactions are quite useful in preparing high yields of nitriles from the corresponding carboxylic acids. However, some acids, such as phthalic, isophthalic, terephthalic, benzoic, and toluic, are difficult to handle because their melting points are quite high, ca. 122°-425°, and they tend to sublime readily from the melt. The actual physical handling of such melts, e.g., metering, pumping, transferring, etc. presents a host of problems requiring special equipment, sophisticated techniques, and constant attention.

Many of these problems could be alleviated if a suitable reaction mixture were used. This invention demonstrates that complexes formed between heterocyclic nitrogen compounds, such as pyridine, quinoline, etc., and tri-substituted amines, such as triethylamine, and carboxylic acids, are useful in overcoming these problems.

The present invention solves the problem of charging the high-melting carboxylic acids, providing thereby a process for converting both low and high-melting carboxylic acids to the corresponding nitriles, by using a carboxylic acid-nitrogenous base complex. Substantially all of the nitrogenous base can be recovered from the reaction mixture because they do not recomplex with the nitriles produced. In addition, the nitrogenous bases are selected such that they do not react with ammonia at the reaction condition.

SUMMARY OF THE INVENTION

Nitriles are prepared from the corresponding carboxylic acids nitrogen base-carboxylic acid complex. Preferably, the complex is reacted with ammonia at a temperature of from about 200° to 800°C. The reaction preferably takes place in the presence of silica gel or alumina. A particularly advantageous feature of nitrogenous invention is the recovery of substantially all of the nitrogenous base, as it does not take part in the nitrile reaction.

UTILITY OF THE INVENTION

Nitriles have great commercial importance as solvents and as chemical intermediates.

DESCRIPTION OF THE PREFERRED EMBODIMENTS

The nitrogenous bases used to form the complexes with carboxylic acids used in the process of this invention have no replaceable hydrogen atoms and are unreactive with the carboxylic acids in the sense of forming amides or nitriles. However, the compounds do react with the acids by forming an acid-base complex as described below. It is preferred that the nitrogenous bases described in this invention be at least about as basic as pyridine and that they be a liquid at ambient temperature (e.g. 20°C). The nitrogenous bases of this invention are tri-substituted at the nitrogen atom and comprise heterocyclic nitrogen compounds such as pyridine and tri-substituted amines.

By "complex" is meant a compound which is made up structurally of two or more compounds or ions, that is, a compound formed by a combination of substances that are themselves capable of independent existence. More specifically, in the present invention, "complex" is used to describe the chemical moiety produced by the interaction of carboxylic acid with nitrogenous base. The chemical literature often describes such complexes as hydrogen-bonded complexes. In most cases, the complexes of the invention are liquids and are thus easily handled. Previous workers have used solids, e.g., the ammonium salt of the acid which has proven to be intractably difficult to handle mechanically because it is a high melting solid. Though the Applicant does not wish to be bound by any particular mechanism hypothesized herein, it seems probable that the liquid complex of the present invention enters the reaction zone and is thereupon virtually immediately disassociated by contact with ammonia as well as by the influence of the temperature of the reaction zone. The reaction with the ammonia then proceeds practically exactly as though the more difficultly handled ammonium salt of the acid had been introduced.

The complexing of the carboxylic acids with the nitrogenous base is believed to be due to the acid-base type reaction as shown in Equation 1,

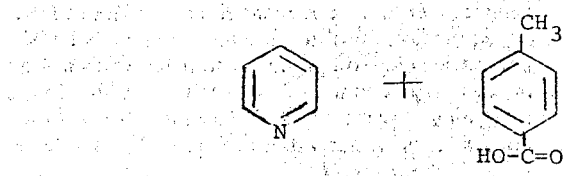 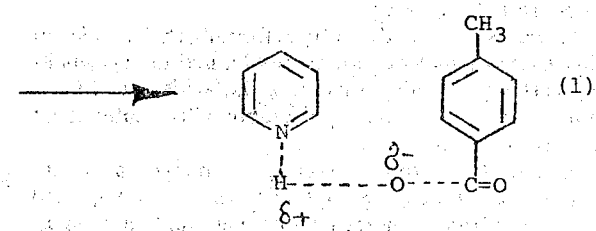

where δ indicates partial charge, the δ+ and δ− denote partially developed charges rather than fully developed or formal charges, e.g., see Jack Hene, *Physical Organic Chemistry*, 2nd Ed., McGraw-Hill Book Co., Inc., (1962) p. 286.

It is theorized that similar complexes are formed between tri-substituted amines and carboxylic acids. It is further theorized that the complex (Equation 1) is broken down when contacted with ammonia at the elevated reaction temperatures. The carboxylic acid is thereby freed for reaction with the ammonia.

It is preferred that the boiling point of the nitrogenous base be low compared to that of the resulting nitrile so that it can be readily separated and recovered by distillation of the reactor effluent. Pyridine is the preferred complexing agent because it has a relatively low boiling point and forms a liquid complex with large amounts of acid, for example, toluic acid forms a liquid complex at room temperature with pyridine containing up to 40 percent of the carboxylic acid.

Thus, this invention teaches production of nitriles from carboxylic acids using a carboxylic acid-nitrogenous base complex as the raw material. The basic nitrogenous compound in the complex is preferably pyridine or an alkyl derivative of pyridine. The nitrogenous base may also be quinoline or alkyl derivative of quinoline. In addition, the nitrogenous base may be a tri-substituted amine. Mixtures of the above mentioned compounds are also suitable for forming complexes. More preferably, the alkyl derivatives of pyridine and quinoline are lower alkyl derivatives containing from 1 to about 6 carbon atoms in the alkyl group(s). Preferably, the tri-substituted amine contains from 1 to about 8 carbon atoms per alkyl substituent. Upon forming the carboxylic acid-nitrogenous base complex, the raw material is preferably contacted with ammonia at a temperature of about 200° to about 800°C., and more preferably from 400° to 600°C. The ammonia may be contacted with the raw material in the presence of an alumina or a silica gel catalyst.

The invention may be practiced in the vapor or liquid phase by maintaining the reaction zone at appropriate pressures to maintain the reactants in the desired phase. The vapor phase will be preferred. The invention can be practiced in the presence of dehydration catalysts, e.g., silica gel, alumina, etc., but such catalysts are not necessary.

The carboxylic acids useful in forming the complex in this invention include, but are not limited to, high-melting carboxylic acids, polycarboxylic acids, and substituted carboxylic acids, preferably alkyl substituted carboxylic acids.

Among the preferred aromatic carboxylic acids are phthalic, isophthalic, terephthalic, benzoic and o, p and m-toluic. Other preferred carboxylic acids are linear $C_4$-$C_{14}$ dicarboxylic acids, such as malonic, succinic, adipic, suberic, pimelic, azelaic, sebasic, undecanedioic, dodecanedioic, tridecanedioic, tetradecanedioic, maleic, fumaric, and citric acids. The mole ratio of the ammonia to the carboxylic acid in the complex is about 3 to about 15 moles of ammonia per mole of carboxylic acid. After contacting the complex with ammonia, the nitriles thus produced are recovered and preferably the nitrogenous base is recycled.

The conditions for forming the complexes themselves are not narrowly critical and will vary according to the particular carboxylic acid and nitrogenous base selected. However, in general, from about 100 to about 1, more preferably from about 10 to about 1, and most preferably from about 1 to about 1 moles of nitrogenous base will be reacted per mole of carboxylic acid and a complex will be formed at a temperature of about −50° to about 200°C, more preferably from about 0° to about 100° and most preferably from about 25° to about 75°C and at a pressure of from about 0.1 to about 100, more preferably from about 0.5 to about 50 and most preferably from about 1 to about 10 atmospheres.

It should be understood that the invention is capable of a variety of modifications and variations which will be made apparent to those skilled in the art.

EXAMPLES

EXAMPLES I–V

A stainless steel, tubular reactor, 36 inches long and 1.0 inches in diameter, is filled with 4–8 mesh silica gel and heated to 480°C. A complex containing equal quantities (by weight) of carboxylic acid and tri-substituted nitrogenous base is then charged to the reactor at a rate of 85.4 ml/hr. Ammonia if fed to the reactor at a rate of 2400 cc/hr. After 4.1 hours, 350 ml of the complex is charged to the reactor. Under these conditions, the following results were noted:

| Example No. | FEED Carboxylic Acid | Wt. % | Tri-Substituted Nitrogenous Base | OUTPUT Nitrile | Recovery | Base Recovery |
|---|---|---|---|---|---|---|
| 1 | p-toulic acid | 50% | pyridine | p-tolunitrile | 91.8% | almost quantitatively |
| 2 | p-tert butyl-benzoic acid | 30% | pyridine | p-tert-butyl-benzonitrile | >90.0% | essentially quantitatively |
| 3 | terephthalic acid | 25% | pyridine | terephthalonitrile | Good | Good |
| 4 | p-toluic acid | 40% | 1,4 dimethyl quinoline | p-tolunitrile | Good | Good |
| 5 | terephthalic acid | 30% | triethylamine | terephthalonitrile | Good | Good |

What is claimed is:

1. A process for producing nitriles from corresponding carboxylic acids, said process comprising in combination:
   a. forming a complex of said carboxylic acid selected from the group consisting of p-toluic, o-toluic, m-toluic, phthalic, isophthalic, terephthalic, benzoic, malonic, succinic, adipic, suberic, pimelic, azelaic, sebasic, undecanedioic, dodecanedioic, tridecanedioic, tetradecanedioic, maleic, fumaric, and citric acids with a nitrogenous base comprising at least one compound selected from the group consisting of pyridine, alkyl derivatives of pyridine, quinoline, alkyl derivatives of quinoline, and mixtures of the foregoing,
   b. contacting said complex with ammonia at a temperature of about 200° to 800°C,
   c. recovering the nitriles thus produced,
wherein about 3 to about 15 moles of ammonia are employed per mole of said carboxylic acid.

2. A process according to claim 1 wherein said ammonia is contacted with said complex compound in the presence of a catalyst selected from the group consisting of silica gel and alumina.

3. A process for producing nitriles from corresponding carboxylic acid, said process comprising:
a. forming a complex of said carboxylic acid and nitrogenous base comprising at least one compound selected from the group consisting of pyridine, alkyl derivatives of pyridine, quinoline, alkyl derivatives of quinoline, tri-substituted amines, and mixtures of the foregoing to form a single-phase reaction mixture,
b. contacting said single-phase reaction mixture with ammonia at a temperature of about 200° to about 800°C,
c. recovering the nitriles thus produced, and
d. recovering the nitrogenous base.

4. A process according to claim 3 wherein the mole ratio of said ammonia to said carboxylic acid in said complex is about 3 to about 15 moles of ammonia per mole of carboxylic acid.

5. A process according to claim 4 wherein said complex is contacted with said ammonia about 400° to about 600°C.

6. A process for producing nitriles from corresponding carboxylic acids selected from the group consisting of p-toluic acid, p-tert butyl-benzoic acid, and terephthalic acid, said process comprising in combination:
a. forming a complex of said carboxylic acid with a nitrogenous base comprising at least one compound selected from the group consisting of pyridine, alkyl derivatives of pyridine, quinoline, alkyl derivatives of quinoline, tri-substituted amines, and mixtures of the foregoing,
b. contacting said complex with ammonia at a temperature of about 200° to about 800°C,
c. recovering the nitriles thus produced.

7. A process for producing nitriles from corresponding carboxylic acids, said process comprising in combination:
a. forming a complex of said carboxylic acid with a nitrogenous base comprising at least one compound selected from the group consisting of pyridine, 1,4 dimethyl quinoline, and triethylamine,
b. contacting said complex with ammonia at a temperature of about 200° to about 800°C,
c. recovering the nitriles thus produced.

8. A process for producing nitriles from corresponding carboxylic acids selected from the group consisting of p-toluic acid, p-tert butyl benzoic acid, and terephthalic acid, said process comprising in combination:
a. forming a complex of said carboxylic acid with a nitrogenous base comprising at least one compound selected from the group consisting of pyridine, 1,4 dimethyl quinoline, and triethylamine,
b. contacting said complex with ammonia at a temperature of about 200° to about 800°C,
c. recovering the nitriles thus produced.

9. A process for producing p-tolunitrile from p-toluic acid, said process comprising in combination:
a. forming a complex of said p-toluic acid with pyridine,
b. contacting said complex with ammonia at a temperature of about 200° to about 800°C,
c. recovering the p-tolunitrile produced.

10. A process for producing p-tert-butyl-benzonitrile from p-tert-butyl benzoic acid, said process comprising in combination:
a. forming a complex of said p-tert-butyl-benzoic acid with pyridine,
b. contacting said complex with ammonia at a temperature of about 200° to about 800°C,
c. recovering the p-tert-butyl-benzonitrile thus produced.

* * * * *

UNITED STATES PATENT OFFICE
CERTIFICATE OF CORRECTION

Patent No. 3,948,968　　　　　　　　　　Dated April 6, 1976

Inventor(s) Roy B. Duke

It is certified that error appears in the above-identified patent and that said Letters Patent are hereby corrected as shown below:

Column 2, lines 1 and 2:　delete "nitrogenous" and substitute therefor --this--

Column 4, line 61:　　　　before "800°C" insert --about--

Signed and Sealed this

Fifth Day of June 1979

[SEAL]

Attest:

RUTH C. MASON
*Attesting Officer*

DONALD W. BANNER
*Commissioner of Patents and Trademarks*